(12) United States Patent
Crabb et al.

(10) Patent No.: US 8,063,213 B2
(45) Date of Patent: Nov. 22, 2011

(54) PRODUCTION OF ROSUVASTATIN CALCIUM SALT

(75) Inventors: Jeffrey Norman Crabb, Bristol (GB); John Horbury, Bristol (GB); Nigel Phillip Taylor, Macclesfield (GB)

(73) Assignee: AstraZeneca UK Limited, London (GB)

(*) Notice: Subject to any disclaimer, the term of this patent is extended or adjusted under 35 U.S.C. 154(b) by 1039 days.

(21) Appl. No.: 10/558,390

(22) PCT Filed: Jun. 3, 2004

(86) PCT No.: PCT/GB2004/002373
§ 371 (c)(1),
(2), (4) Date: Feb. 29, 2008

(87) PCT Pub. No.: WO2004/108691
PCT Pub. Date: Dec. 16, 2004

(65) Prior Publication Data
US 2008/0221323 A1    Sep. 11, 2008

(30) Foreign Application Priority Data

Jun. 5, 2003  (GB) .................. 0312896.4
Oct. 24, 2003  (GB) .................. 0324793.9

(51) Int. Cl.
*C07D 239/36* (2006.01)
*C07D 239/42* (2006.01)

(52) U.S. Cl. .............. 544/332; 544/331; 544/330

(58) Field of Classification Search ............ 544/322
See application file for complete search history.

(56) References Cited

U.S. PATENT DOCUMENTS

| | | | |
|---|---|---|---|
| 4,645,858 A | 2/1987 | Lowrie et al. | |
| 4,970,313 A | 11/1990 | Wess et al. | |
| 4,977,279 A | 12/1990 | Wess et al. | |
| 5,026,698 A | 6/1991 | Fujikawa et al. | |
| 5,260,440 A * | 11/1993 | Hirai et al. | 544/332 |
| 5,278,313 A | 1/1994 | Thottathil et al. | |
| 5,399,722 A | 3/1995 | Beck et al. | |
| 5,594,153 A | 1/1997 | Thottathil et al. | |
| 6,278,001 B1 | 8/2001 | Solladie et al. | |
| 6,331,641 B1 | 12/2001 | Taoka et al. | |
| 6,784,171 B2 | 8/2004 | Taylor et al. | |
| 6,841,554 B2 * | 1/2005 | Taylor et al. | 514/275 |
| 6,844,437 B1 | 1/2005 | Taylor et al. | |
| 6,870,059 B2 | 3/2005 | Kooistra et al. | |
| 6,875,867 B2 | 4/2005 | Brodfuehrer et al. | |
| 7,129,352 B2 * | 10/2006 | Taylor et al. | 544/297 |
| 7,157,255 B2 | 1/2007 | Blacker et al. | |
| 7,304,156 B2 | 12/2007 | Matsushita et al. | |
| 7,416,865 B2 | 8/2008 | Blacker et al. | |
| 7,442,811 B2 | 10/2008 | Bakel Van et al. | |
| 7,511,140 B2 * | 3/2009 | Horbury et al. | 544/297 |
| 7,524,955 B2 | 4/2009 | Newton et al. | |
| 7,642,363 B2 | 1/2010 | Kooistra et al. | |
| 7,718,812 B2 | 5/2010 | Hof | |
| 7,732,171 B2 | 6/2010 | Blacker et al. | |
| 7,816,528 B2 | 10/2010 | Matsushita et al. | |
| 7,842,807 B2 | 11/2010 | Horbury et al. | |
| 7,888,083 B2 | 2/2011 | Blacker et al. | |
| 2003/0018199 A1 | 1/2003 | Brodfuehrer et al. | |
| 2003/0114685 A1 | 6/2003 | Niddam-Hildesheim et al. | |
| 2005/0124639 A1 | 6/2005 | Joshi et al. | |
| 2005/0209259 A1 | 9/2005 | Huang | |
| 2006/0004200 A1 | 1/2006 | Gudipati et al. | |
| 2006/0293355 A1 | 12/2006 | Booth et al. | |
| 2007/0105882 A1 | 5/2007 | Black et al. | |
| 2007/0255060 A1 | 11/2007 | Okada et al. | |
| 2008/0188657 A1 | 8/2008 | Lenger | |
| 2008/0207903 A1 | 8/2008 | Butters et al. | |

(Continued)

FOREIGN PATENT DOCUMENTS

CA    2545316    5/2005

(Continued)

OTHER PUBLICATIONS

Kaneko et al. "Preparation of optically active 5,6-epoxyhexanoic acid esters as materials for physiologically active substances" Chemical Abstracts + Indexes, American Chemical Society, Columbus, US 118(11):832 (1993).

(Continued)

*Primary Examiner* — Venkataraman Balasubramanian
(74) *Attorney, Agent, or Firm* — Morgan Lewis & Bockius LLP

(57) ABSTRACT

An improved process for the manufacture of (E)-7-[4-(4-flurophenyl)-6-isopropyl-2-[methyl(methylsulfony)amino]pyrimidin-5-yl](3R,5S)-3,5-dihydroxyhept-6-enoic acid calcium salt, Formula (1), which is useful for the production of a pharmaceutical useful in the treatment of, inter alia, hypercholesterolemia, hyperlipoproteinemia and atherosclerosis, is described.

Formula (1)

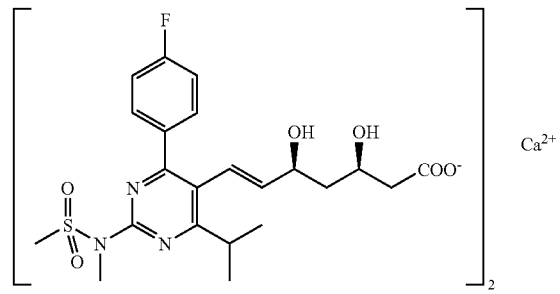

13 Claims, No Drawings

U.S. PATENT DOCUMENTS

| | | |
|---|---|---|
| 2008/0221323 A1 | 9/2008 | Crabb et al. |
| 2009/0264654 A1 | 10/2009 | Newton et al. |
| 2010/0136339 A1 | 6/2010 | Kooistra et al. |
| 2010/0222373 A1 | 9/2010 | Booth et al. |
| 2010/0228028 A1 | 9/2010 | Butters et al. |

FOREIGN PATENT DOCUMENTS

| | | |
|---|---|---|
| EP | 0521471 | 1/1993 |
| EP | 0521471 | 10/2000 |
| WO | WO 90/03973 | 4/1990 |
| WO | WO 93/08823 | 5/1993 |
| WO | WO 97/03959 | 2/1997 |
| WO | WO 97/19917 | 6/1997 |
| WO | WO 97/49681 | 12/1997 |
| WO | WO 00/42024 | 7/2000 |
| WO | WO 00/49014 | 8/2000 |
| WO | WO 01/22962 | 4/2001 |
| WO | WO 01/36384 | 5/2001 |
| WO | WO 01/54669 | 8/2001 |
| WO | WO 01/60804 | 8/2001 |
| WO | WO 01/72706 | 10/2001 |
| WO | WO 01/85702 | 11/2001 |
| WO | WO 01/85975 | 11/2001 |
| WO | WO 02/06266 | 1/2002 |
| WO | WO 02/30415 | 4/2002 |
| WO | WO 02/43667 | 6/2002 |
| WO | WO 02/43732 | 6/2002 |
| WO | WO 02/072566 | 9/2002 |
| WO | WO 02/083637 | 10/2002 |
| WO | WO 02/098854 | 12/2002 |
| WO | WO 03/006439 | 1/2003 |
| WO | WO 03/016317 | 2/2003 |
| WO | WO 03/018555 | 3/2003 |
| WO | WO 03/026573 | 4/2003 |
| WO | WO 03/059901 | 7/2003 |
| WO | WO 03/087112 | 10/2003 |
| WO | WO 03/097614 | 11/2003 |
| WO | WO 03/106447 | 12/2003 |
| WO | WO 2004/014872 | 2/2004 |
| WO | WO 2004/052867 | 6/2004 |
| WO | WO 2004/054986 | 7/2004 |
| WO | WO 2004/089895 | 10/2004 |
| WO | WO 2004/103977 | 12/2004 |
| WO | WO 2004/108691 | 12/2004 |
| WO | WO 2005/005384 | 1/2005 |
| WO | WO 2005/023778 | 3/2005 |
| WO | WO 2005/023779 | 3/2005 |
| WO | WO 2005/028450 | 3/2005 |
| WO | WO 2005/030215 | 4/2005 |
| WO | WO 2005/040134 | 5/2005 |
| WO | WO 2005/042522 | 5/2005 |
| WO | WO 2005/047276 | 5/2005 |
| WO | WO 2005/051921 | 6/2005 |
| WO | WO 2005/054207 | 6/2005 |
| WO | WO 2005/056534 | 6/2005 |
| WO | WO 2005/063728 | 7/2005 |
| WO | WO 2005/068435 | 7/2005 |
| WO | WO 2005/077916 | 8/2005 |
| WO | WO 2005/077917 | 8/2005 |
| WO | WO 2005/092867 | 10/2005 |
| WO | WO 2006/017357 | 2/2006 |
| WO | WO 2006/035277 | 4/2006 |
| WO | WO 2006/067456 | 6/2006 |
| WO | WO 2006/079611 | 8/2006 |
| WO | WO 2006/089401 | 8/2006 |
| WO | WO 2007007119 | 1/2007 |

OTHER PUBLICATIONS

Menges et al. "Oxidative Degradation of γ-Butyrolactons into 1,3-Diols via a Criegee Rearrangement of Peroxosulfonates. An Enantioselective Synthesis of Compactin Lactone and its Diastereomer" Synlett 12:901-905 (1993).

Presentation given at the 20th International Congress of Heterocyclic Chemistry in Palermo, Aug. 1-5, 2005.

Presentation given at the Gordon Conference on Heterocyclic Compounds, Salve Regina University, Newport, Rhode Island, Jul. 4-9, 2004.

Sakaki et al. "Lipase-catalyzed asymmetric synthesis of 6-(3-chloro-2-hydroxypropyl)-1,3-dioxin-4-ones and their conversion to chiral 5,6-epoxyhexanoates" Tetrahedron: Asymmetry 2(5):343-346 (1991).

Shao et al. "Asymmetric hydrogenation of 3,5-Dioxoesters catalyzed by Ru-binap complex: A short step asymmetric synthesis of 6-substituted 5,6-dihydro-2-pyrones" Tetrahedron 49(10):1997-2010 (1993).

Watanabe et al. "Synthesis and Biological Activity of Methanesulfonamide Pyrimidine- and N-Methanesulfonyl Pyrrole-Substituted 3,5-Dihydroxy-6-heptenoates, a Novel Series of HMG-CoA Reductase Inhibitors" Bioorganic & Medicinal Chemistry 5(2):437-444 (1997).

Moore et al. "Biosynthesis of the hypocholesterolemic agent mevinolin by *Aspergillus terreus*. Determination of the origin of carbon, hydrogen, and oxygen atoms by carbon-13 NMR and mass spectrometry" J. Am. Chem. Soc. 107(12): 3694-3701 (1985).

Hiyama et al. "Syntheis of Artificial HMG-CoA Reductase Inhibitors Based on the Olefination Strategy" Bull. Chem. Soc. Jpn. 68 (1):364-372 (1995).

Minami et al. "A Novel Enantioselective Synthesis of HMG Co-A Reductase Inhibitor NK-104 and a Related Compound" Tetrahedron letters 33(49):7525-7526 (1992).

Minami et al. "Stereoselective Reduction of β,-Diketo Esters Derived From Tartaric Acid. A Facile Route to Optically Active 6-oxo-3,5-syn-isopropylidenedioxyhexanoate, a Versatile Synthetic Intermediate of Artificial HMG Co-A Reductase Inhibitors" Tetrahedron Letters 34(3):513-516 (1993).

Prasad et al. "A novel diastereroselective synthesis of lactone moiety of compactin" Tetrahedron Letters 25(23):2435-2438 (1984).

Solladié et al. "Chrial Sulfoxides in Asymmetric Synthesis: Enantioselective Synthesis of the Lactonic Moiety of (+)-Compactin and (+)-Mevinolin. Application of a Cornpactin Analogue" J. Org. Chem. 60:7774-7777 (1995).

Wess et al. "Stereoselective Synthesis of HR 780 A New Highly Potent HMG-CoA Reductase Inhibitor", Tetrahedron Letters 31(18): 2545-2548 (1990).

Nezasa et al. "Pharmacokinetics and disposition of rosuvastatin, a new 3-hydroxy-3-methylglutaryl coenzyme A reductase inhibitor, in rat" Xenobiotica 32(8):715-727 (2002).

* cited by examiner

PRODUCTION OF ROSUVASTATIN CALCIUM SALT

The present application is a U.S. National Phase Application of International Application No. PCT/GB2004/002373 (filed Jun. 3, 2004) which claims the benefit of GB Patent Application No. 0312896.4 (filed Jun. 5, 2003) and GB Patent Application No. 0324793.9 (filed Oct. 24, 2003), all of which are hereby incorporated by reference in their entireties.

This invention concerns improvements to a chemical process, particularly a chemical process for manufacture of (E)-7-[4-(4-fluorophenyl)-6-isopropyl-2[methyl(methylsulfonyl)amino]pyrimidin-5-yl](3R,5S)-3,5-dihydroxyhept-6-enoic acid calcium salt (1) (illustrated below), which is useful for the production of a pharmaceutical useful in the treatment of, inter alia, hypercholesterolemia, hyperlipoproteinemia and atherosclerosis.

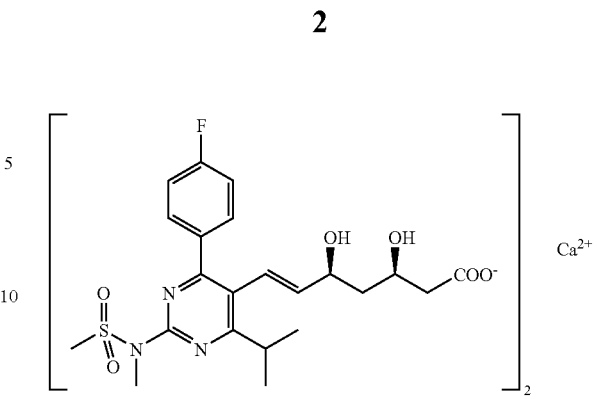

The sodium salt (2) and calcium salt (1) of compound (E)-7-[4-(4-fluorophenyl)-6-isopropyl-2-[methyl(methylsulfonyl)amino]pyrimidin-5-yl](3R,5S)-3,5-dihydroxyhept-6-enoic acid (hereinafter referred to as the 'Agent') were disclosed in European Patent 0521471. This patent also describes a process for the synthesis of the calcium salt (1), via the sodium salt (2), as shown in Scheme 1 below. The calcium salt thus formed is then collected and dried and may be processed further as required.

Scheme 1

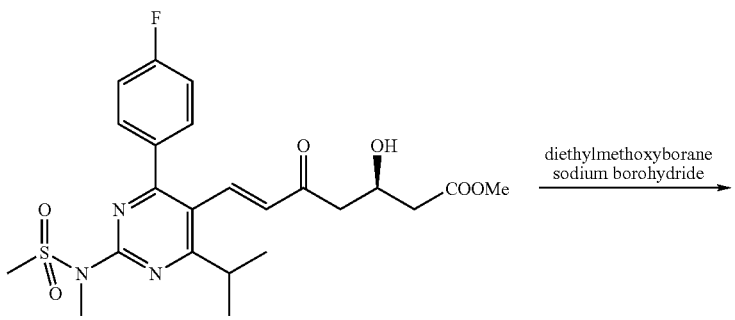

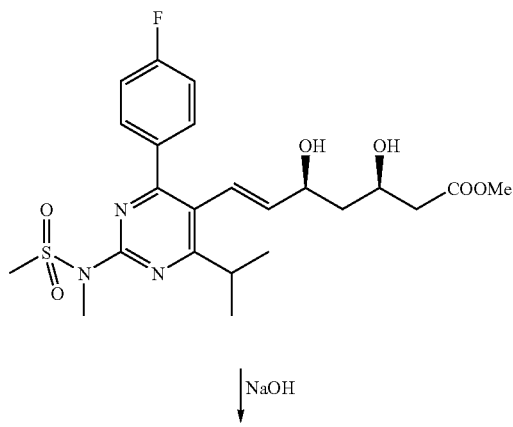

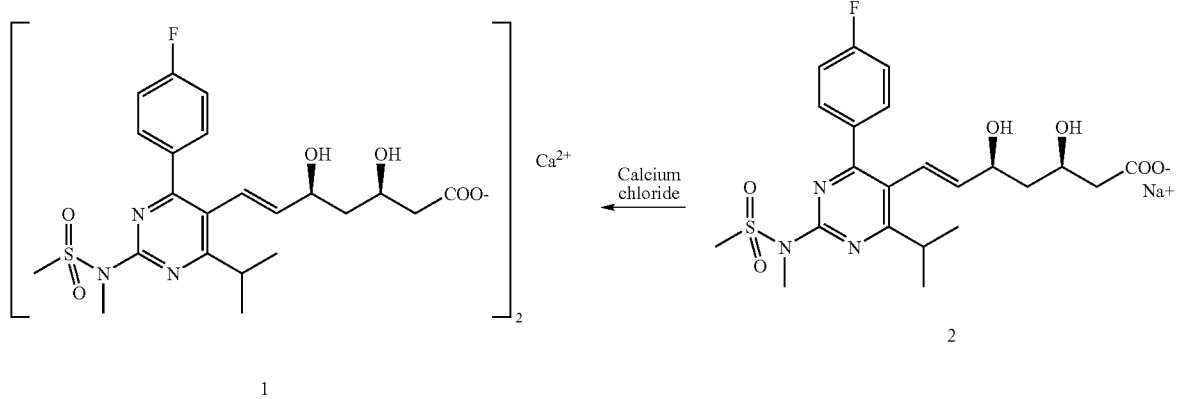
Our International Patent Application WO 00/49014 describes an alternative route to the calcium salt (1), also via the sodium salt (2), from the compound BEM (3), which is exemplified as shown in Scheme 2 below:
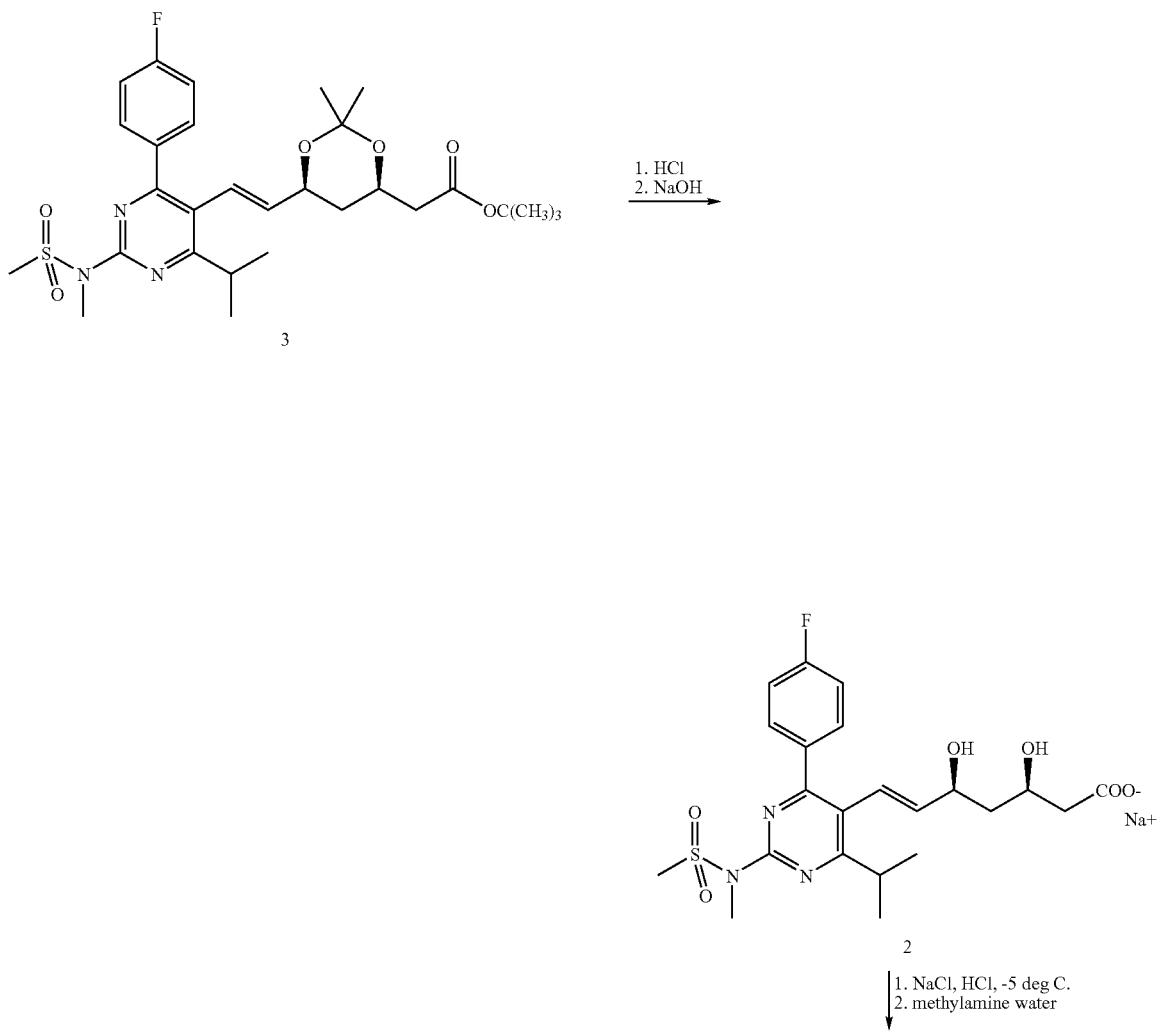

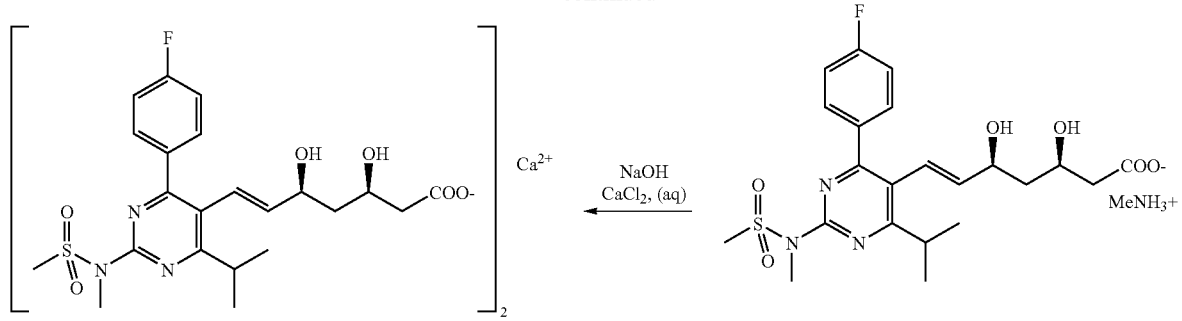

As described in WO 00/49014, the transformation from BEM (3) to the calcium salt (1) may be carried out via the methylamine salt (4) as shown in Scheme 2. Isolation of this intermediate crystalline methylamine salt allows purification by recrystallisation before final formation of the (amorphous) calcium salt.

Our co-pending application WO 2004/014872 describes an improved process for isolation of the calcium salt from a water soluble salt, such as the transformation from the methylamine salt (4) to the calcium salt (1) in Scheme 2 above, wherein the improvement comprises adjustment of time and temperature parameters such that optimal physical form of the product is obtained.

We have surprisingly discovered an improvement to the process of manufacturing the calcium salt, which results in improved overall yield and a reduced number of steps to effect the transformation from BEM (3) to the calcium salt (1), whereby the step of isolating an intermediate salt is avoided. Surprisingly the quality of the resultant calcium salt product is not adversely affected. The process of this invention is also applicable to alkyl esters of the agent other than the tertiary-butyl ester, BEM (3).

According to the present invention there is provided an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a) to g):
a) reaction of a (1-6C)alkyl ester of (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetic acid in a water miscible organic solvent with aqueous acid at an elevated temperature;
b) reaction of the resulting solution with an aqueous alkali metal hydroxide and optionally washing the resulting aqueous alkali metal salt solution with a suitable organic solvent;
c) adjustment of the pH of the resulting solution to between pH6 and pH11;
d) removal of the water miscible organic solvent;
e) optional filtration of the resulting mixture;
f) addition of a water soluble calcium salt to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt; and
g) isolation of the product of step f).

It will be appreciated that this process achieves the conversion of the ester to the calcium salt (1) without isolation of an intermediate salt of the acid.

Step a)
Suitable solvents for step a) are in general any water miscible organic solvent; for example solvents such as acetonitrile and acetone. A preferred solvent is acetonitrile.

Suitable aqueous acids are acids whose calcium salt is water soluble so that it is not precipitated in Step f). In one embodiment, the aqueous acid is hydrochloric acid. In one aspect of this embodiment, the aqueous hydrochloric acid is approximately 0.1M. In another aspect of this embodiment, the aqueous hydrochloric acid is ≦ about 0.1M. Conveniently the aqueous hydrochloric acid is <0.05M, for example 0.02M.

Suitably, the reaction of the (1-6C)alkyl ester of the Agent with aqueous acid is carried out between 30 and 50° C., conveniently between 35 and 40° C.

More suitably, the (1-6C)alkylester of the Agent, dissolved in acetonitrile at 35° C. is reacted with aqueous hydrochloric acid at 35° C.

Suitable (1-6C)alkyl esters of the Agent are, for example methyl, ethyl, propyl, isopropyl, n-butyl, iso-butyl, pentyl or hexyl esters. BEM is a preferred example of a (1-6C)alkyl ester of (E)-7-[4-(4-fluorophenyl)-6-isopropyl-2-[methyl (methylsulfonyl)amino]pyrimidin-5-yl](3R,5S)-3,5-dihydroxyhept-6-enoic acid.

The starting material BEM may be made as described in WO 00/49014. Analogues of BEM may be made by analogous processes, as illustrated in the Examples hereinafter.

Step b)
Step b) may be carried out at a temperature of between approximately 10° C. and approximately 40° C. Conveniently, step b) is carried out at ambient temperature, which will generally be understood to mean 20-25° C., conveniently approximately 25° C.

Suitably the aqueous alkali metal hydroxide is aqueous potassium hydroxide or aqueous sodium hydroxide.

In one embodiment, the aqueous alkali metal hydroxide is sodium hydroxide. In this embodiment, suitably the aqueous sodium hydroxide is about 1M and sufficient quantity is added to form the sodium salt (2). It will be appreciated that the sodium salt (2) is not isolated and that the product of step b) is an aqueous sodium salt solution. It will also be appreciated that this aqueous sodium salt solution also contains acetonitrile.

The aqueous alkali metal salt solution may be washed with toluene, or another suitable organic solvent to remove unreacted (1-6C)alkyl ester of the Agent, such as BEM (3), or other unwanted minor components if required, prior to carrying out step c). Suitable organic solvents for this washing step are in general organic solvents which are immiscible in water but miscible with the water miscible organic solvent used in step a). When the water miscible organic solvent in step a) is acetonitrile, suitable organic solvents for the washing step are ester, ether and hydrocarbon solvents known in the art. Examples of such suitable solvents are xylene (hydrocarbon solvent), methyl-t-butylether (MTBE) (ether solvent) and ethyl acetate (ester solvent). The toluene or other suitable organic solvent may conveniently be removed from the process by phase separation. Any solvent remaining after phase separation may be removed in Step d). Preferably the solvent is toluene.

In one embodiment, the aqueous alkali metal salt is an aqueous sodium salt. In this embodiment, in step b), the aqueous sodium salt solution is washed with a suitable organic solvent. In one aspect of this embodiment, the aqueous sodium salt solution is washed with toluene, xylene, MTBE or ethyl acetate. In a further aspect of this embodiment, the aqueous sodium salt solution is washed with toluene or xylene. In a further aspect of this embodiment, the aqueous sodium salt solution is washed with toluene. In a further aspect of this embodiment, the aqueous sodium salt solution is washed with MTBE. In a further aspect of this embodiment, the aqueous sodium salt solution is washed with ethyl acetate.

In another embodiment, in step b), the aqueous sodium salt solution is not washed with a suitable organic solvent.

In an alternative embodiment of this invention, the aqueous alkali metal hydroxide is potassium hydroxide. It will be appreciated that in this embodiment, the potassium salt equivalent of the sodium salt (2) is formed as a result. In this embodiment, suitable temperatures, concentrations of potassium hydroxide and washing solvents are those described as suitable for sodium hydroxide hereinbefore.

Step c)

Adjustment of the aqueous solution to pH 6-11 is suitably carried out by addition of hydrochloric acid, for example 0.02 to 1M aqueous hydrochloric acid. In one embodiment, the solution is adjusted to pH 8-11. In another embodiment, the solution is adjusted to pH 9-11, for example about pH 9-10.5. Suitably, the solution is adjusted to about pH 9-10.5 using ≦0.1M hydrochloric acid. More suitably, the solution is adjusted to about pH 10.5 using about 0.1M hydrochloric acid. Preferably the solution is adjusted to about pH9, suitably using 0.02M aqueous hydrochloric acid. Other inorganic acids known in the art may also be used, provided the calcium salt of the inorganic acid is water soluble so that it is not precipitated in Step f).

Step d)

The water miscible organic solvent (and residual amounts of any organic solvent used as a wash in step b) above), may generally be removed by distillation, conveniently carried out under vacuum.

When the water miscible organic solvent is acetonitrile, the distillation is suitably carried out for example using a vacuum of ≦55 mBar, and a temperature of ≦45° C. Conveniently, the vacuum is about 52 mBar and the temperature is about 33° C. It will be appreciated by those skilled in the art that water may be azeotropically removed with the acetonitrile during the distillation and that it may therefore be desirable to add further water to the mixture during the distillation process. A suitable method for carrying out the distillation is provided in the accompanying non-limiting Example.

Step e)

Filtration of the mixture resulting from step d) removes any unreacted starting material or insoluble impurities which may have precipitated during the distillation process of step d). It will be appreciated that water may be used to wash the filter. Any filter known in the art to be suitable may be used. Conveniently at a manufacturing scale, a GaF filter may be used (for example, a GAP filter E6-1825, manufactured by "Haywood Industrial Products).

It will be appreciated that this filtration is not always necessary and may be omitted.

Step f)

Generally, the water soluble calcium salt is suitably any such salt whose counter-ion forms a water soluble salt with sodium, such that it is easily removed by washing the product after isolation in step g). Suitable water soluble calcium salts include calcium chloride, calcium bromide and calcium acetate. More suitably, calcium chloride or calcium bromide is used.

In one embodiment, the water soluble calcium salt is calcium chloride.

In this embodiment, calcium chloride is conveniently provided as its dihydrate form and is suitably added to the filtrate as an aqueous solution. A slight excess of calcium chloride may be used, for example 0.6 molar equivalents compared to the Agent. The calcium chloride is suitably added as a 0.1 g/ml aqueous solution. The temperature of the reaction mixture is suitably maintained at 32-43° C., more suitably at approximately 40° C., during the addition process. The rate of addition of calcium chloride may be adjusted such that the temperature of the reaction mixture is so maintained. Suitably the calcium chloride is added over 15-30 minutes. The mixture may be maintained at the addition temperature for a period (herein referred to as the 'hold time') before isolation of the calcium salt. In one embodiment, the hold time is at least 10 minutes. In another embodiment the hold time is at least 20 minutes. In a further embodiment the hold time is at least 30 minutes.

Step g)

Isolation of the calcium salt may conveniently be carried out by filtration, conveniently at about 20° C. (herein referred to as the "filtration temperature"). The mixture may be maintained at the filtration temperature for a period before filtration is carried out, for example for 10 to 20 minutes, conveniently for 15 minutes. It will be appreciated that water may be used to wash the filtrate.

According to the present invention there is provided an improved process for the formation of (E)-7-[4-(4-fluorophenyl)-6-isopropyl-2-[methyl(methylsulfonyl)amino]pyrimidin-5-yl](3R,5S)-3,5- dihydroxyhept-6-enoic acid calcium salt, which comprises the steps a) to g):

a) reaction of tert-butyl (E)-(6-{2-[4-(4-fluorophenyl)-6-isopropyl-2-[methyl(methylsulfonyl)amino]pyrimidin-5-yl]vinyl }(4R,6S)-2,2-dimethyl[1,3]dioxan-4-yl)acetate (BEM) in acetonitrile with aqueous hydrochloric acid at an elevated temperature;
b) reaction of the resulting solution with aqueous sodium hydroxide;
c) adjustment of the pH of the resulting solution to between pH6 and pH11;
d) removal of acetonitrile;
e) filtration of the resulting mixture;
f) addition of calcium chloride to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt; and
g) isolation of the product of step f).

In a further aspect of the invention there is provided an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a), b) c), d), f) and g) as described hereinbefore.

According to the present invention is provided an improved process for the formation of (E)-7-[4-(4-fluorophenyl)-6-isopropyl-2-[methyl(methylsulfonyl)amino]pyrimidin-5-yl] (3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyriridin-5-yl]vinyl}(4R,6S)-2,2-dimethyl[1,3]dioxan4-yl)acetic acid in acetonitrile with aqueous hydrochloric acid at an elevated temperature;

b) reaction of the resulting solution with aqueous sodium hydroxide;

c) adjustment of the pH of the resulting solution to between pH6 and pH11;

d) removal of acetonitrile;

e) filtration of the resulting mixture;

f) addition of calcium chloride to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt; and g) isolation of the product of step f).

In a further aspect of the invention is provided an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a'), b) c), d), f) and g) as described hereinbefore.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a) to g):

a) reaction of tert-butyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate (BEM) in acetonitrile with aqueous hydrochloric acid at 35-40° C;

b) reaction of the resulting solution with 1M sodium hydroxide at ambient temperature and optionally washing the resulting aqueous sodium salt solution with a suitable organic solvent;

c) adjustment of the pH of the resulting solution to about pH9 by addition of <0.05M aqueous hydrochloric acid;

d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetic acid in acetonitrile with aqueous hydrochloric acid at 35-40° C.;

b) reaction of the resulting solution with 1M sodium hydroxide at ambient temperature and optionally washing the resulting aqueous sodium salt solution with a suitable organic solvent;

c) adjustment of the pH of the resulting solution to about pH9 by addition of <0.05M aqueous hydrochloric acid;

d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a) to g):

a) reaction of tert-butyl (E)-(6-{2-[4-(4-fluorophenyl)-6-isopropyl-2-[methyl(methylsulfonyl)amino]pyrimidin-5-yl]vinyl }(4R,6S)-2,2-dimethyl[1,3]dioxan-4-yl)acetate (BEM) in acetonitrile with aqueous hydrochloric acid at 35-40° C.;

b) reaction of the resulting solution with 1M sodium hydroxide at ambient temperature and optionally washing the resulting aqueous sodium salt solution with a suitable organic solvent;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl }(4R,6S)-2,2-dimethyl[1,3]dioxan-4-yl)acetic acid in acetonitrile with aqueous hydrochloric acid at 35-40° C.;

b) reaction of the resulting solution with 1M sodium hydroxide at ambient temperature and optionally washing the resulting aqueous sodium salt solution with a suitable organic solvent;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetic acid in acetonitrile with aqueous hydrochloric acid at 35-40° C.;

b) reaction of the resulting solution with 1M sodium hydroxide at ambient temperature and optionally washing the resulting aqueous sodium salt solution with a suitable hydrocarbon, ester or ether solvent;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan4-yl)acetic acid in acetonitrile with aqueous hydrochloric acid at 35-40° C.;

b) reaction of the resulting solution with 1M sodium hydroxide at ambient temperature and optionally washing the resulting aqueous sodium salt solution with toluene, xylene, MTBE or ethylacetate;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl) amino]pyrimidin-5-yl]vinyl}(4R,6S)-2,2-dimethyl [1,3]dioxan-4-yl)acetic acid in acetonitrile with aqueous hydrochloric acid at 35-40° C.;

b) reaction of the resulting solution with 1M sodium hydroxide at ambient temperature and optionally washing the resulting aqueous sodium salt solution with toluene;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetic acid in acetonitrile with aqueous hydrochloric acid at 35-40° C.;

b) reaction of the resulting solution with 1M sodium hydroxide at ambient temperature and washing the resulting aqueous sodium salt solution with a suitable hydrocarbon, ester or ether solvent;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5- dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl }(4R,6S)-2,2-dimethyl[1,3]dioxan-4-yl)acetic acid in acetonitrile with aqueous hydrochloric acid at 35-40° C.;

b) reaction of the resulting solution with 1M sodium hydroxide at ambient temperature and washing the resulting aqueous sodium salt solution with toluene, xylene, MTBE or ethylacetate;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g):

a') reaction of a (1-6C)alkyl ester of (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetic acid in acetonitrile with aqueous hydrochloric acid at 35-40° C.;

b) reaction of the resulting solution with 1M sodium hydroxide at ambient temperature and washing the resulting aqueous sodium salt solution with toluene;

c) adjustment of the pH of the resulting solution to about pH 9-10.5 using ≦0.1M aqueous hydrochloric acid d) removal of acetonitrile by distillation at 50-55 mBar and 30-35° C.;

e) filtration of the resulting mixture;

f) addition of an aqueous solution of calcium chloride dihydrate to the filtrate so as to form (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, at 32-43° C.; and g) isolation of the product of step f) by filtration at about 20° C.

In a further embodiment, the present invention provides an improved process for the formation of (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt, which comprises the steps a') to g) as described in any aspect or embodiment hereinbefore or hereinafter, wherein, in step b), potassium hydroxide is used instead of sodium hydroxide.

The process of the invention generally results in improved overall percentage yield (starting from BEM or other (1-6C) alkyl ester) and a reduced number of steps in comparison with the processes known in the art. It will be appreciated that a higher percentage yield may provide a significant cost benefit when manufacture is taking place on a commercial scale. The reduced number of steps in the process of the invention results in fewer operational processes during the manufacture, which may translate into a more robust process. The reduced number of steps in the process of the invention involves reduced handling of material, which may result in less opportunity for degradation or contamination of the product. Also, certain chemical reagents are no longer required and the total amount of waste and/or effluent is reduced, providing an environmental benefit.

A further aspect of the invention provides the compound (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt made by the process steps a) to g) as hereinbefore described.

A further aspect of the invention provides the compound (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt made by the process steps a') to g) as described in any aspect or embodiment hereinbefore.

Therefore a further aspect of the invention provides a product obtainable by the process of the present invention.

Another aspect of the invention provides a product obtained by the process of the present invention.

It will be appreciated that the process of the current invention could be applied to make alternative salts of the Agent, such as the magnesium salt by use of a suitable magnesium salt in step f), such as magnesium chloride. Such a salt thus obtained could be converted by processes known in the art into the calcium salt (1). Thus in another aspect of the invention, is provided a process for making the magnesium salt of the Agent, comprising the steps a) to g) as hereinbefore described wherein, in step f) a water soluble magnesium salt (such as magnesium chloride) is added instead of a water soluble calcium salt (such as calcium chloride).

The invention is further illustrated by the following examples.

EXAMPLE 1

BEM (20.0 g) was dissolved in acetonitrile (140 ml) at 40° C., then cooled to 35° C. before gradual addition of hydrochloric acid (0.02M, 35 ml) at 35° C. The resulting solution was stirred at 35° C. until the reaction was complete then cooled to 25° C. Sodium hydroxide (1.0M, 38 ml) was added at 25° C. and the resulting mixture stirred at this temperature until the reaction was complete. Aqueous hydrochloric acid (1M) was added to adjust the pH of the solution to pH9. The solution was distilled under reduced pressure (52 mBar, ≦40° C.) until approximately 100 ml of acetonitrile/water had been removed. Water (100 ml) was added and distillation continued until a further 100 ml of acetonitrile/water had been removed. The resulting mixture was filtered through a filter pad, the filter washed with water (30 ml) and the filtrates heated to 40° C. before addition of a solution of calcium chloride dihydrate (3.07 g) in water (29.5 ml) over 20 min, maintaining the reaction mixture at 38-41° C. The reaction mixture was stirred for a further 15 min at 40° C., then cooled to 20° C. and stirred at this temperature for a further 15 min. The resulting suspension was filtered, washed with water (3×50 ml) and dried to give (E)-7-[4-(4-fluorophenyl)-6-isopropyl-2[methyl(methylsulfonyl)amino]pyrimidin-5-yl](3R,5S)-3,5-dihydroxyhept-6-enoic acid calcium salt (15.8 g, 84% yield).

EXAMPLE 2

The synthesis of analogues of BEM is illustrated below for the iso-propyl analogue. Other analogues can be made by similar procedures.

iso-Propyl (E)-(6-{2-[4-(4-fluorophenyl)-6-isopropyl-2-[methyl(methylsulfonyl)amino]pyrimidin-5-yl]vinyl}(4R,6S)-2,2-dimethyl[1,3]dioxan-4-yl)acetate Sodium bis(trimethylsilyl)amide (80.47 mL, 1.0M in THF) was added dropwise to a cooled solution of diphenyl [4-(4-fluoropheny)-6-isopropyl-2-[methyl(methylsulfonyl)amino]pyrimidin-5-ylmethyl] phosphine oxide (40.43 g, 75 mmol) in ThF (477.1 mL) at −65° C. over 30 minutes, maintaining the temperature at −65° C. Isopropyl-2-[(4R,6S)-6-formyl-2,2-dimethyl-1,3-dioxan-4-yl] acetate in toluene (21.68 g) was added dropwise to the solution over 35 minutes, maintaining the temperature at −65° C. The contents of the vessel were kept at −65° C. for 15 minutes, then allowed to warm evenly to 10° C. over 80 minutes. Water (40.4 mL) followed by acetic acid (6.87 g, 114 mmol) were added to give a two phase light yellow solution. The batch was then distilled at atmospheric pressure to remove ~485 mL of distillates. This solution was washed sequentially with water (84 mL), 7.0% w/w sodium bicarbonate (92.6 g), 1.8% w/w sodium bicarbonate (91.1 g) and water (63.5 mL). The resulting organic phase was distilled under vacuum at 270 mbar to leave ~95 mL of solution in the distillation flask (removing ~229 mL of distillates). Methanol (202 mL) at 50° C. was charged to the flask and the solution distilled at atmospheric pressure, removing ~134 mL of distillates. A further portion of methanol (229 mL) at 50° C. was added to the solution and the batch cooled to 40° C. over 30 minutes. The batch was cooled to 25° C. over 30 minutes, 0-5° C. over 30 minutes, then chilled to −8° C. over 20 minutes and kept at this temperature for 30 minutes. The solid was collected by vacuum filtration, washed with 2 portions of cooled (−8° C.) methanol (2×80.6 mL) then dried in a vacuum oven at 50° C., 200 mbar, yield=28.9 g (68.3%).

$^1$H NMR δ: 1.15 (q, 1H) 1.24 (dd, 6H) 1.27 (dd, 6H) 1.40 (s, 3H) 1.49 (s, 3H) 1.55 (dt, 1H) 2.34 (dd, 1H) 2.50 (dd, 1H) 3.38 (spt, 1H) 3.51 (s, 3H) 3.57 (s, 3H) 4.32 (m, 1H) 4.43 (m, 1H) 5.04 (spt, 1H) 5.47 (dd, 1H) 6.52 (d, 1H) 7.08 (t, 2H) 7.65 (dd, 2H)

Isopropyl-2-[(4R,6S)-6-formyl-2,2-dimethyl-1,3-dioxan-4-yl}acetate

Chlorine gas (2469.6 mL, 118 mmol) was charged to toluene (373.3 mL, 16 rel vol) at −60° C. Dimethyl sulphide (11.67 mL, 121 mmol) was then added dropwise to the cooled solution over 30 minutes, keeping the contents at −60° C. After 30 minutes at this temperature, isopropyl 2-[(4R,6S)-6-hydroxymethyl-2,2-dimethyl-1,3-dioxan4-yl}acetate (24.56 g, 95 mmol) in toluene (46.7 mL) was added dropwise to the vessel over 30 minutes, maintaining the internal temperature at −60° C. The reaction mixture was agitated at −60° C. for 30 minutes followed by the dropwise addition of triethylamine (26.36 g, 261 mmol) over 30 minutes, allowing the internal temperature to rise to −50° C. The reaction mixture was then allowed to warm to 25° C. evenly over 75 minutes. The resulting slurry was stirred at 25° C. for 30 minutes, then water (77 mL) was added and the mixture agitated for 30 minutes. The aqueous layer was separated and the pH checked (pH should be between 7.5 and 8.5). The resulting organic portion was washed with water (23.3 mL) and the organic portion separated for vacuum distillation at 150 mbar. Distillation was continued until ~350 mL of toluene had been removed. Toluene (350 mL) was added to the flask and the vacuum distillation repeated at 150 mbar to remove ~350 mL of toluene. The resulting solution was transferred to a flask containing activated 4 angstrom molecular sieves and left at ambient temperature overnight. This solution was used directly for the coupling stage.

Iso-propyl 2-[(4R,6S)-6-hydroxymethyl-2,2-dimethyl-1,3-dioxan-4-yl}acetate

This compound may be made using the procedures described in EP0319847. Analogues with different ester groups R may be made by a similar method.

Diphenyl [4-(4-fluoropheny)-6-isopropyl-2-[methyl (methylsulfonyl)amino]pyrimidin-5-ylmethyl] phosphine oxide This compound can be made as described in Patent Application WO00/49014

EXAMPLE 3

Procedure using Wash in step b)

BEM (20.0 g) was dissolved in acetonitrile (140 ml) at 40° C., then cooled to 35° C. before gradual addition of hydrochloric acid (0.02M, 35 ml) at 35° C. The resulting solution was stirred at 35° C. until the reaction was complete then cooled to 25° C. Further acetonitrile (8 ml) was added before sodium hydroxide (1.0M, 38 ml) was added at 25° C. and the resulting mixture stirred at this temperature until the reaction was complete. Aqueous hydrochloric acid (0.1M) was added to adjust the pH of the solution to approximately pH10.5. Water was added so that the combined volume of water and hydrochloric acid (0.1M) (from the previous pH adjustment step) added was 100 ml. Toluene (125 ml) was then added and the mixture stirred at 40° C. for 30 minutes before it was allowed to settle for 1 hour at 40° C. The aqueous phase was then separated from the organic phase at 40° C. The aqueous phase was distilled under reduced pressure (53 mBar, ≦40° C.) until the volume was reduced to 135 ml. The resulting aqueous solution was filtered through a filter pad and the filter washed with water and combined with the aqueous reaction solution, such that the total volume of the resulting aqueous solution was 170 ml. This solution was heated to 40° C. before addition of a solution of calcium chloride di-hydrate (3.05 g) in water (29.5 ml) over 20 min, maintaining the reaction mixture at 38-41° C.

The reaction mixture was stirred for a further 15 min at 40° C., then cooled to 20° C. and stirred at this temperature for a further 15 min. The resulting suspension was filtered, washed with water (3×53 ml) and dried to give (E)-7-[4-(4-fluorophenyl)-6-isopropyl-2-[methyl(methylsulfonyl)amino]pyrimidin-5-yl](3R,5S)-3,5-dihydroxyhept-6-enoic acid calcium salt (14.7 g @100% strength, 85% yield).

$^1$H NMR δ: 1.21 (d+d, 6H) 1.32 (dt, 1H) 1.51 (dt, 1H) 2.00 (dd, 1H) 2.14 (dd, 1H) 3.42 (spt, 1H)* 3.45 (s, 3H) 3.54 (s, 3H) 3.77 (m, 1H) 4.21 (q, 1H) 5.53 (dd, 1H) 6.51 (dd, 1H) 7.27 (t, 2H) 7.71 (dd, 2H)

[The 1H NMR was carried out as a 3% w/v solution in $d^6$ DMSO (where $d^5$ DMSO=2.51 δ)]. *partially obscured

The invention claimed is:
1. A process for the formation of (E)-7-[4-(4-fluorophenyl)-6-isopropyl-2-[methyl (methylsulfonyl)amino]pyrimidin-5-yl](3R,5S)-3,5-dihydroxyhept-6-enoic acid calcium salt, comprising the steps a) to g):
   a) reacting a (1-6C)alkyl ester of (E)-(6-{2-[4-(4-fluorophenyl)-6-isopropyl-2-[methyl(methylsulfonyl) amino]pyrimidin-5-yl]vinyl}(4R,6S)-2,2-dimethyl[1,3]dioxan-4-yl) acetic acid in a water miscible organic solvent with aqueous acid at a temperature of 30-50° C.;
   b) reacting the resulting solution with an aqueous alkali metal hydroxide and optionally washing the resulting aqueous alkali metal salt solution with a suitable organic solvent;
   c) adjusting the pH of the resulting solution to between pH 9 and pH 10.5 by addition of aqueous hydrochloric acid;
   d) removing the water miscible organic solvent;
   e) optionally filtering the resulting mixture;
   f) adding a water soluble calcium salt to the filtrate so as to form (E)-7-[4-(4-fluorophenyl)-6-isopropyl-2-[methyl (methylsulfonyl)amino]pyrimidin-5-yl](3R,5S)-3,5-dihydroxyhept-6-enoic acid calcium salt; and
   g) isolating the product of step f).
2. The process as claimed in claim 1 wherein the water miscible organic solvent is acetonitrile.
3. The process as claimed in claim 1 wherein in step a) the aqueous acid is hydrochloric acid.
4. The process as claimed in claim 1 wherein step b) comprises:
   reacting the resulting solution with aqueous sodium hydroxide and washing the resulting aqueous sodium salt solution with an organic solvent selected from the group consisting of a hydrocarbon solvent, an ester solvent and an ether solvent.

5. The process as claimed in claim 1 wherein the aqueous sodium salt solution is washed with an organic solvent selected from the group consisting of toluene, xylene, MTBE and ethyl acetate.

6. The process as claimed in claim 5 wherein the aqueous sodium salt solution is washed with toluene.

7. The process as claimed in claim 1 wherein the (1-6C) alkyl ester is tert-butyl ester.

8. The process as claimed in claim 1 wherein step a) is carried out at 35-40° C.

9. The process as claimed in claim 1 wherein step b) is carried out at ambient temperature.

10. The process as claimed in claim 1 wherein in step b), the aqueous alkali metal hydroxide is potassium hydroxide.

11. The process as claimed in claim 1 wherein step d) is carried out at a pressure of $\leqq 55$ mBar and a temperature of $\leqq 45°$ C.

12. The process as claimed in claim 1 wherein in step f) the water soluble calcium salt is calcium chloride.

13. The process as claimed in claim 1 wherein in step f) the calcium salt is added at 32-43° C.

* * * * *